United States Patent [19]
Gaffney et al.

[11] Patent Number: 5,985,934
[45] Date of Patent: Nov. 16, 1999

[54] SYNERGISTIC ANTIMICROBIAL COMPOSITION OF 2,4,4'-TRICHLORO-2'-HYDROXYDIPHENYL ETHER AND 1,2-DIBROMO-2,4-DICYANOBUTANE

[75] Inventors: Tammy W. Gaffney, Pittsburgh; Allan L. Melby, Cranberry Township, both of Pa.

[73] Assignee: Calgon Corporation, Pittsburgh, Pa.

[21] Appl. No.: 08/636,101

[22] Filed: Apr. 22, 1996

[51] Int. Cl.$^6$ .............................. A01N 31/14; A01N 37/34
[52] U.S. Cl. ............................................ 514/672; 514/721
[58] Field of Search ................................. 514/672, 721; 424/405

[56] References Cited

U.S. PATENT DOCUMENTS

| | | | |
|---|---|---|---|
| 3,644,380 | 2/1972 | Harmetz et al. | 260/294.9 |
| 3,833,731 | 9/1974 | Grier et al. | 424/304 |
| 3,833,743 | 9/1974 | Morse et al. | 426/195 |
| 3,873,597 | 3/1975 | Harmetz et al. | 260/465.7 |
| 3,877,922 | 4/1975 | Grier et al. | 71/67 |
| 3,929,858 | 12/1975 | Swigert | 260/465.7 |
| 4,442,122 | 4/1984 | Engelhart et al. | 424/304 |
| 4,496,581 | 1/1985 | Engelhart et al. | 514/438 |
| 4,604,405 | 8/1986 | Jakubowski | 514/526 |
| 4,655,815 | 4/1987 | Jakubowski | 71/67 |
| 4,675,178 | 6/1987 | Klein et al. | 424/65 |
| 4,830,657 | 5/1989 | Jakubowski et al. | 71/67 |
| 5,034,405 | 7/1991 | Jakubowski | 514/369 |
| 5,124,355 | 6/1992 | Tully et al. | 514/526 |
| 5,364,874 | 11/1994 | Morpeth | 514/373 |

*Primary Examiner*—Phyllis G. Spivack
*Attorney, Agent, or Firm*—Diane R. Meyers; Eckert Seamans Cherin & Mellott, LLC

[57] ABSTRACT

Synergistic antimicrobial combinations consisting essentially of comprising 2,4,4'-trichloro-2'-hydroxydiphenyl ether and 1,2-dibromo-2,4-dicyanobutane are disclosed. Methods for inhibiting microbial growth using these synergistic antimicrobial combinations are also disclosed.

13 Claims, No Drawings

SYNERGISTIC ANTIMICROBIAL COMPOSITION OF 2,4,4'-TRICHLORO-2'-HYDROXYDIPHENYL ETHER AND 1,2-DIBROMO-2,4-DICYANOBUTANE

BACKGROUND OF THE INVENTION

1. Field of the Invention

The present invention relates to synergistic antimicrobial compositions which are generally useful for inhibiting microbial growth wherever such microbial growth is found, for example, in aqueous systems related to a wide variety of industrial applications. More particularly, the present invention relates to synergistic admixtures of 2,4,4'-trichloro-2'-hydroxydiphenyl ether and 1,2-dibromo-2,4-dicyanobutane. Methods for using the same are also disclosed.

2. Description of the Background Art

Both 2,4,4'-trichloro-2'-hydroxydiphenyl ether, referred to herein as Triclosan, and 1,2-dibromo-2,4-dicyanobutane (DBDCB), are known individually as antimicrobial agents. The unexpected finding of the present invention is that they are synergistic when used in combination. As used herein, the terms "synergy" and "synergistic" refer to instances where the effectiveness of a composition comprising two or more biocides, such as Triclosan and DBDCB, exceeds the sum of the efficacies of the individual components taken alone. Thus, using a synergistic biocidal combination may allow for use of a lower overall concentration of biocide or the realization of an enhanced antimicrobial effect at a comparable dosage.

U.S. Pat. Nos. 3,833,731, 3,877,922, 3,873,597, 3,644,380, 3,833,743, and 3,929,858 disclose DBDCB and its use as an antibacterial, antifingal, and algicidal agent. Compounds related to DBDCB are also effective as antimicrobial agents. For example, U.S. Pat. No. 4,442,122 describes the use of 1,2-dibromo-2-cycloalkane compounds to inhibit microbial growth, and U.S. Pat. No. 4,496,581 discloses 1,2-dibromo-2-cyano-2-(heterocyclic) alkane compounds and their use as antimicrobial agents.

The use of DBDCB and related compounds in conjunction with other antimicrobial agents is also known in the art. U.S. Pat. No. 4,604,405 describes a synergistic antimicrobial composition for industrial and agricultural use comprised of DBDCB and 2,2-dibromo-3-nitrilopropionamide. U.S. Pat. No. 4,655,815 discloses a synergistic antimicrobial admixture comprising DBDCB and a formaldehyde donor. U.S. Pat. No. 4,830,657 describes a synergistic antimicrobial combination comprising DBDCB and 1,2-benzisothiazolin-3-one. U.S. Pat. No. 5,034,405 discloses the use of admixtures of DBDCB, 2-methyl-4-isothiazolin-3-one and 5-chloro-2-methyl-4-isothiazolin-3-one as antimicrobial agents. U.S. Pat. No. 5,124,355 discloses an antimicrobial composition of DBDCB and 2-(decylthio) ethaneamine and a method of using the same. U.S. Pat. No. 5,364,874 discloses a composition containing 2-halo-2-halomethylglutaronitrile and a 4,5-polymethylene-4-isothiazolin-3-one which has antibacterial and antifungal effects.

Likewise, the use of 2,4,4'-trichloro-2'-hydroxydiphenyl ether and related compounds, both alone and in conjunction with other biocides, is known. The synergistic combination of Triclosan and DBDCB, however, is not taught or suggested in the art.

As used herein, the phrases "antimicrobial", "biocide", and "inhibiting microbial growth" refer to the killing of, the inhibition of, or the control of the growth of bacteria, yeast, mold, and/or algae. A number of important industries have experienced serious adverse effects from the activity of such biological growth on the raw materials which they employ, in their process waters, on various components of their manufacturing processes, and in the finished products which they produce. Such industries include the paint, wood, textile, cosmetic and personal care, leather, tobacco, fur, rope, paper, pulp, plastics, fuel, oil, rubber, and machine industries.

It is contemplated that the synergistic admixture of Triclosan and DBDCB as disclosed herein, and the methods for using the same, will be useful in virtually any aqueous system or on any article or product of manufacture in which inhibition of microbial growth is desired, absent compatibility problems. Important applications of the synergistic antimicrobial combinations of the present invention include, for example: inhibiting the growth of bacteria and fungi, including yeast and mold, in aqueous paints, adhesives, latex emulsions, inks and joint cements; preserving wood; preserving cutting oils and metal working fluids; controlling slime-producing bacteria and fungi, including yeast and mold, in pulp and paper mills and cooling towers; as a spray or dip treatment for textiles and leather to prevent mold growth; as a component of anti-fouling paints to prevent adherence of fouling organisms; protecting paint films, especially exterior paints, from attack by fungi which occurs during weathering of the paint film; protecting processing equipment from slime deposits during manufacture of cane and beet sugar, foods, foodstuffs and food additives; preventing microorganism buildup and deposits in air washer or scrubber systems and in industrial fresh water supply systems; controlling microorganism contamination in closed loop and recirculating water cooling systems; controlling microorganism contamination and deposits in oil field drilling fluids and muds, and in secondary petroleum recovery processes; preventing bacterial and fungal growth in paper coating processes which might adversely affect the quality of the paper coating; controlling bacterial and fungal growth and deposits during the manufacture of various specialty boards, e.g., cardboard and particle board; preventing sap stain discoloration on freshly cut wood of various kinds; controlling bacterial and fungal growth in clay and pigment slurries of various types which are manufactured for later use in paper coating and paint manufacturing and which are susceptible to degradation by microorganisms during storage and transport; as a hard surface disinfectant to prevent growth of bacteria and fungi on walls, floors, etc.; and in swimming pools to prevent algal growth.

The synergistic antimicrobial composition disclosed in the present invention is particularly applicable to the control of bacterial and fungal growth in cosmetic and personal care products. Such products include but are not limited to creams, lotions, shampoos, conditioners, sunscreens, hand cleaners, liquid hand soaps, detergents, hospital scrubs, bactericidal washes, deodorants, and the like. Cosmetic and personal care products subject to microbiological attack can suffer from separation of emulsions, discoloration, unsightly visible colonies, malodor, and change of pH; microbial growth in these products can also lead to potential health hazards.

Accordingly, there remains a very real and substantial need for antimicrobial compositions capable of effectively controlling and/or inhibiting microbial growth in industrial aqueous systems and in articles of manufacture. Because of increasing environmental regulations, there is still a further need to provide biocidal compositions having enhanced antimicrobial effect which are effective in lower doses than historically used. Use of lower amounts of biocides has a favorable impact on the environment, and allows users to realize significant cost savings.

SUMMARY OF THE INVENTION

The present invention generally meets the above described needs by providing synergistic antimicrobial combinations comprising 2,4,4'-trichloro-2'-hydroxydiphenyl ether (Triclosan) and 1,2-dibromo-2,4-dicyanobutane (DBDCB). The present invention also provides a method for inhibiting microbial growth in aqueous systems and on articles of manufacture prone to such growth comprising adding to said systems or applying to said articles an effective amount of Triclosan and DBDCB.

As used herein, the term "effective amount" refers to that amount of a composition comprising Triclosan and DBDCB necessary to achieve the desired level of inhibition or control of microbial growth in the aqueous system or on the article being treated.

DESCRIPTION OF THE INVENTION

The present invention is directed to a synergistic antimicrobial composition comprising: a) 2,4,4'-trichloro-2'-hydroxydiphenyl ether; and b) 1,2-dibromo-2,4-dicyanobutane, wherein the weight ratio of a) to b), on an active basis, ranges from about 1000:1 to 1:1000. The present insention is further directed to a method for inhibiting microbial growth in an aqueous svstem or on an article of manufacture prone to such growth, which method comprises treating said system or said article with an effective amount of an antimicrobial combination of: a) 2,4,4'-trichloro-2'-hydroxydiphenyl ether and b) 1,2-dibromo-2,4-dicyanobutane, wherein the weight ratio of a) to b), on an active basis, ranges from about 1000:1 to 1:1000.

In accordance with the present invention, the weight ratio of the two components of the synergistic combination are dictated by the dosage levels of each component which demonstrate synergism, based on 100% active ingredient, relative to each end use application. Typically, the weight ratio of component a), Triclosan, and component b), DBDCB, ranges from about 1000:1 to 1:1000 on an active basis, preferably from about 100:1 to 1:500, more preferably from about 4:1 to 1:64. As will be understood by one skilled in the art, however, the synergistic weight ratio of the two components generally varies to some extent depending on the application and the organism being controlled. For example, a higher ratio of Triclosan to DBDCB might be more effective in one application, while a higher ratio of DBDCB to Triclosan might be more effective in another application. The Triclosan/DBDCB composition has been found particularly effective against bacteria when used in a weight ratio of between about 4:1 and 1:16.

An effective amount of a synergistic combination of Triclosan and DBDCB should be added to the aqueous system being treated. At least 0.1 parts per million (ppm), based on the weight of water in the system being treated, of the synergistic combination described above is added. Preferably, between about 1 ppm and about 10,000 ppm of Triclosan and between about 10 ppm and 2000 ppm of DBDCB, based on the weight of water in the system being treated, are added. More preferably, between about 50 ppm and 1000 ppm of Triclosan and between about 100 ppm and 500 ppm of DBDCB, based on the weight of water in the system being treated, are added. It is well within the ordinary skill of one practicing in the art to determine the effective amount of biocide for a given system based on various system parameters including but not limited to the size of the system, pH of the system, the types of organisms present and the amount of control desired.

Likewise, an effective amount of a synergistic combination of Triclosan and DBDCB should be applied to the article of manufacture being treated. Generally, a solution of the synergistic antimicrobial combination described above having a concentration of at least 0.1 ppm is incorporated into, sprayed onto, used to dip, or otherwise applied to the substrate being treated in order to prevent growth of bacteria, mold, yeast and algae. Again, it is well within the ordinary skill of one practicing in the art to determine the effective amount of biocide to apply to a given article of manufacture being treated.

The active ingredients of the synergistic antimicrobial compositions of the present invention may be used in diverse formulations: solid, including finely divided powders and granular materials; as well as liquid, such as solutions, emulsions, suspensions, concentrates, emulsifiable concentrates, slurries and the like, depending upon the application intended, and the formulation media desired. Further, when the synergistic antimicrobial combinations are liquid, they may be employed neat or may be incorporated into various formulations, both solid and liquid, as an adsorbate on suitable inert carriers such as talc, clays, diatomaceous earth and the like, or water and various organic liquids such as lower alkanols, kerosene, benzene, toluene, and other petroleum distillate fractions or mixtures thereof. Triclosan is commercially available in powder form from Ciba Geigy, Greensboro, N.C., as Irgasan®DP 300. DBDCB is commercially available from Calgon Corporation, Pittsburgh, Pa. in various forms, including solid, liquid and aqueous dispersions.

It will also be understood by one skilled in the art that the synergistic antimicrobial combination disclosed herein may be used in combination with other antimicrobial materials. For example, the combination can be combined with other fungicides and bactericides in appropriate concentrations and in appropriate instances so as to combine the action of each to obtain particularly useful results. Such combinations might find particular application in the preparation of germicidal soaps, in the production of cosmetics and aqueous coatings and in combating paper mill slime accumulations. The synergistic antimicrobial combination of the present invention can be combined with other algicidal agents as well.

In accordance with the present invention there is still further provided a method of inhibiting the growth of at least one of: bacteria, yeast, mold and algae. According to the methods of the present invention, this growth is inhibited in aqueous systems or on articles or products of manufacture prone to such growth. These methods comprise adding to the aqueous system or treating the article or product containing said bacteria, yeast, mold and/or algae with an effective amount of a synergistic combination of Triclosan and DBDCB. This addition can be accomplished either by simple addition of Triclosan and DBDCB together as a single admixture, or by addition of the two components separately. Such separate administration can either bc at the same time or at different times. The net effect will be the same—the system, article or product being treated will ultimately have incorporated therein or have applied thereto the desired dosage concentration of each component.

Further, the compositions of the present invention are believed to be effective irrespective of the method of application. For example, the antimicrobial compositions described herein can be added to a system being treated via a low level, continuous feed practice, a semi-continuous feed practice or through slug feeding. All of these feeding practices will be familiar to one having ordinary skill in the art. Slug feeding is particularly effective and therefore is a preferred manner of employing the methods of the present invention. In a recirculating water system, slug feeding allows the user to monitor the microorganism concentration in the system, and feed product only when microorganism concentrations increase; the user realizes a cost savings by feeding an effective amount of Triclosan and DBDCB only when needed. Typically, when treating a cosmetic or personal care product, a slug feed should be added to the product at the end of the manufacturing process after the product has cooled to below about 50° C.

As noted above, the present invention is based upon the discovery that use of Triclosan in conjunction with DBDCB produces synergistic results and is effective in controlling the growth of bacteria, yeast, mold and algae in a variety of industrial and other applications. The utility of the synergistic antimicrobial combination disclosed herein derives from its versatility both in the numerous industries in which it can be applied, as well as the numerous microorganisms against which it is effective.

The superior antimicrobial activity of the synergistic antimicrobial combination of Triclosan and DBDCB has been confirmed using standard laboratory techniques. The antimicrobial combination has been found effective, for example, in inhibiting microbial growth including but not limited to the bacteria *Klebsiellapneumoniae, Escherichia coli* and *Pseudomonas aeruginosa*, and the yeast *Candida albicans*. The combination is also believed to be effective against other bacteria, such as Bacillus sp., Staphlococcus sp., Flavobacterium sp., Enterobacter sp., and Xanthomonas sp., anaerobic bacteria, other fresh water organisms such as filamentous bacteria, fungi including but not limited to various species of Candida and Saccharomyces and white and pink yeasts, and various species of algae.

EXAMPLES

The following examples are set forth to illustrate the present invention and should not be construed as limiting the invention in any way.

Example 1

The biocidal efficacy in microtiter tests of the antimicrobial composition of the present invention is demonstrated below using *Pseudomonas aeruginosa* (ATCC 15442).

An 8× stock solution of DBDCB was prepared by dissolving about 3.2 grams (g) of 20% active DBDCB in about 4 ml of methanol and diluting the volume up to about 100 ml with deionized water. The DBDCB used in the examples was obtained from Calgon Corporation, Pittsburgh, Pa., as Merguard® 1200. A Triclosan 4× stock solution was prepared by dissolving about 0.16 g of about 99% active Triclosan in about 5 ml of methanol and diluting the volume up to about 100 ml with deionized water. The Triclosan was obtained from Ciba Geigy as Irgasan®DP 300.

Two microtiter plates were prepared for use in the example, each microtiter plate having 8 rows, A–H, and 12 columns, 1–12. The amount of each biocide in each well of the plates is depicted below.

TABLE 1

AMOUNT OF EACH BIOCIDE IN WELLS OF FIRST MICROTITER PLATE

| ROW | | CONCENTRATIONS (ppm Active) | | | | | | | | | | | |
| --- | --- | --- | --- | --- | --- | --- | --- | --- | --- | --- | --- | --- | --- |
| LETTER | BIOCIDE | 1 | 2 | 3 | 4 | 5 | 6 | 7 | 8 | 9 | 10 | 11 | 12 |
| A | DBDCB | 800 | 800 | 800 | 800 | 800 | 800 | 800 | 800 | 800 | 800 | — | 800 |
|   | Triclosan | 400 | 400 | 200 | 200 | 100 | 100 | 50 | 50 | 25 | 25 | — | 0 |
| B | DBDCB | 400 | 400 | 400 | 400 | 400 | 400 | 400 | 400 | 400 | 400 | — | 400 |
|   | Triclosan | 400 | 400 | 200 | 200 | 100 | 100 | 50 | 50 | 25 | 25 | — | 0 |
| C | DBDCB | 200 | 200 | 200 | 200 | 200 | 200 | 200 | 200 | 200 | 200 | — | 200 |
|   | Triclosan | 400 | 400 | 200 | 200 | 100 | 100 | 50 | 50 | 25 | 25 | — | 0 |
| D | DBDCB | 100 | 100 | 100 | 100 | 100 | 100 | 100 | 100 | 100 | 100 | — | 100 |
|   | Triclosan | 400 | 400 | 200 | 200 | 100 | 100 | 50 | 50 | 25 | 25 | — | 0 |
| E | DBDCB | 50 | 50 | 50 | 50 | 50 | 50 | 50 | 50 | 50 | 50 | — | 50 |
|   | Triclosan | 400 | 400 | 200 | 200 | 100 | 100 | 50 | 50 | 25 | 25 | — | 0 |
| F | DBDCB | 25 | 25 | 25 | 25 | 25 | 25 | 25 | 25 | 25 | 25 | — | 25 |
|   | Triclosan | 400 | 400 | 200 | 200 | 100 | 100 | 50 | 50 | 25 | 25 | — | 0 |
| G | DBDCB | 12.5 | 12.5 | 12.5 | 12.5 | 12.5 | 12.5 | 12.5 | 12.5 | 12.5 | 12.5 | — | 12.5 |
|   | Triclosan | 400 | 400 | 200 | 200 | 100 | 100 | 50 | 50 | 25 | 25 | — | 0 |
| H | DBDCB | 0 | 0 | 0 | 0 | 0 | 0 | 0 | 0 | 0 | 0 | — | 0 |
|   | Triclosan | 400 | 400 | 200 | 200 | 100 | 100 | 50 | 50 | 25 | 25 | — | 0 |

The amount of biocide in each well of the second microtiter plate of each set was a follows:

TABLE 2

AMOUNT OF EACH BIOCIDE IN WELLS OF SECOND MICROTITER PLATE

| ROW LETTER | BIOCIDE | CONCENTRATIONS (ppm Active) | | | | | | | | | | | |
|---|---|---|---|---|---|---|---|---|---|---|---|---|
| | | 1 | 2 | 3 | 4 | 5 | 6 | 7 | 8 | 9 | 10 | 11 | 12 |
| A | DBDCB | 800 | 800 | 800 | 800 | 800 | 800 | 800 | 800 | 800 | 800 | — | 800 |
| | Triclosan | 12.5 | 12.5 | 6.25 | 6.25 | 3.125 | 3.125 | 1.56 | 1.56 | 0.78 | 0.78 | — | 0 |
| B | DBDCB | 400 | 400 | 400 | 400 | 400 | 400 | 400 | 400 | 400 | 400 | — | 400 |
| | Triclosan | 12.5 | 12.5 | 6.25 | 6.25 | 3.125 | 3.125 | 1.56 | 1.56 | 0.78 | 0.78 | — | 0 |
| C | DBDCB | 200 | 200 | 200 | 200 | 200 | 200 | 200 | 200 | 200 | 200 | — | 200 |
| | Triclosan | 12.5 | 12.5 | 6.25 | 6.25 | 3.125 | 3.125 | 1.56 | 1.56 | 0.78 | 0.78 | — | 0 |
| D | DBDCB | 100 | 100 | 100 | 100 | 100 | 100 | 100 | 100 | 100 | 100 | — | 100 |
| | Triclosan | 12.5 | 12.5 | 6.25 | 6.25 | 3.125 | 3.125 | 1.56 | 1.56 | 0.78 | 0.78 | — | 0 |
| E | DBDCB | 50 | 50 | 50 | 50 | 50 | 50 | 50 | 50 | 50 | 50 | — | 50 |
| | Triclosan | 12.5 | 12.5 | 6.25 | 6.25 | 3.125 | 3.125 | 1.56 | 1.56 | 0.78 | 0.78 | — | 0 |
| F | DBDCB | 25 | 25 | 25 | 25 | 25 | 25 | 25 | 25 | 25 | 25 | — | 25 |
| | Triclosan | 12.5 | 12.5 | 6.25 | 6.25 | 3.125 | 3.125 | 1.56 | 1.56 | 0.78 | 0.78 | — | 0 |
| G | DBDCB | 12.5 | 12.5 | 12.5 | 12.5 | 12.5 | 12.5 | 12.5 | 12.5 | 12.5 | 12.5 | — | 12.5 |
| | Triclosan | 12.5 | 12.5 | 6.25 | 6.25 | 3.125 | 3.125 | 1.56 | 1.56 | 0.78 | 0.78 | — | 0 |
| H | DBDCB | 0 | 0 | 0 | 0 | 0 | 0 | 0 | 0 | 0 | 0 | — | 0 |
| | Triclosan | 12.5 | 12.5 | 6.25 | 6.25 | 3.125 | 3.125 | 1.56 | 1.56 | 0.78 | 0.78 | — | 0 |

As is illustrated in the table above, the amounts of DBDCB and Triclosan were varied in a serial dilution ranging from 800 ppm active to 12.5 ppm active for DBDCB and 400 ppm active to 0.78 for Triclosan.

The minimum inhibitory concentration (MIC) for each biocide combination against Ps. aeruginosa was determined. The MIC is the least amount of biocide needed to prevent growth in the well, with growth being defined as turbidity in the medium or a "pellet" of cells which came out of the medium and settled at the bottom of the well.

Additional plates were then subcultured from the MIC plates at 24 hours following biocide addition. Subculturing was done to determine the minimum biocidal concentration (MBC). The MBC is the lowest concentration of biocide that results in no growth after subculturing and subsequent incubation.

All of the microtiter plates including the MIC plates and the MBC plates were incubated for 24 hours at 37° C. Following the 24 hour incubation period, the presence or absence of growth in each well of the plates was determined. Growth in the microtiter plates was determined with a Dynatech MR-5000 microplate reader, available from Dynatech Laboratories, Chantilly, Va., the use of which will be familiar to one having ordinary skill in the art. The presence or absence of growth in each well, along with the concentration of biocide in each well, was then used to determine the synergistic properties of the biocide combinations. The synergistic properties were evaluated by determining the Kull value, or K value. The method for calculating K value is well known to those skilled in the art. In this example, the K value was determined by the following formula:

$$K = \frac{[DBDCB] \text{ In Combination}}{[DBDCB] \text{ Alone}} + \frac{[Triclosan] \text{ In Combination}}{[Triclosan] \text{ Alone}}$$

where "[DBDCB] In Combination" means the concentration of DBDCB which, when used in combination with Triclosan, resulted in inhibition of microbial growth;

"[Triclosan] In Combination" means the concentration of Triclosan which, when used in combination with DBDCB, resulted in inhibition of microbial growth;

"[DBDCB] Alone" means the concentration of DBDCB which, when used alone, resulted in inhibition of microbial growth; and "[Triclosan] Alone" means the concentration of the Triclosan which, when used alone, resulted in inhibition of microbial growth.

A K value of less than 1 indicates synergy between the two biocides, a K value of greater than 1 indicates antagonism between the two biocides, and a K value equal to 1 indicates an additive effect of the two biocides.

The K values determined for Pseudomonas aeruginosa are recorded in Table 3.

TABLE 3

"K" VALUES OBTAINED FOR PSEUDOMONAS AERUGINOSA

| [DBDCB] Alone, ppm | [Triclosan] Alone, ppm | [DBDCB] In Combination, ppm | [Triclosan] In Combination, ppm | K Value | Weight Ratio Triclosan:DBDCB |
|---|---|---|---|---|---|
| 200 | 100 | 12.5 | 50 | 0.56 | 4:1 |
| 200 | 100 | 50 | 25 | 0.5 | 1:2 |
| 200 | 100 | 50 | 3.125 | 0.28 | 1:16 |
| 200 | 100 | 100 | 3.125 | 0.53 | 1:32 |
| 200 | 100 | 100 | 1.56 | 0.516 | 1:64 |

As can be seen from the results of Table 3, synergy was demonstrated against *Pseudomonas aeruginosa.*

Example II

Example I was repeated with the following differences. The DBDCB was tested at the following concentrations: 200, 100, 50, 25, 12.5, 6.25 and 3.125, with concentration given in ppm active. The Triclosan stock solution was prepared by dissoling 0.08 g of Irgasan®DP 300, obtained from Ciba Geigy, in about 5 ml of methanol and diluting to 100 ml with deionized water. The Triclosan was tested at the following concentrations: 100, 50, 25, 12.5, 6.25, 3.125, 1.56, 0.78, 0.39 and 0.195, with concentration given in ppm active. The biocidal composition was tested against both the bacterium *Pseudomonas aeruginosa* (ATCC 15442) and the yeast *Candida albicans* (ATCC 10231). The bacterial plates were incubated at 35° C. for 24 hours and the yeast plates at 30° C. for 5 days. Results are presented in Tables 4 and 5 below.

TABLE 4

"K" VALUES OBTAINED FOR *PSEUDOMONAS AERUGINOSA*

| [DBDCB] Alone, ppm | [Triclosan] Alone, ppm | [DBDCB] In Combination, ppm | [Triclosan] In Combination, ppm | K Value | Weight Ratio Triclosan:DBDCB |
|---|---|---|---|---|---|
| 100 | >100 | 25 | 50 | <0.75 | 2:1 |
| 100 | >100 | 50 | 25 | <0.75 | 1:2 |
| 200 | >100 | 100 | 50 | <1.0 | 1:2 |

TABLE 5

"K" VALUES OBTAINED FOR *CANDIDA ALBICANS*

| [DBDCB] Alone, ppm | [Triclosan] Alone, ppm | [DBDCB] In Combination, ppm | [Triclosan] In Combination, ppm | K Value | Weight Ratio Triclosan:DBDCB |
|---|---|---|---|---|---|
| 100 | 12.5 | 3.125 | 6.25 | 0.53 | 2:1 |
| 100 | 12.5 | 6.25 | 6.25 | 0.56 | 1:1 |
| 100 | 12.5 | 12.5 | 6.25 | 0.625 | 1:2 |
| 100 | 12.5 | 25 | 6.25 | 0.75 | 1:4 |
| 100 | 12.5 | 50 | 3.125 | 0.75 | 1:16 |

What is claimed is:

1. A synergistic antimicrobial combination consisting essentially of:
    a) 2,4,4'-trichloro-2'-hydroxydiphenyl ether; and
    b) 1,2-dibromo-2,4-dicyanobutane; as active ingredients wherein the weight ratio of a) to b), on an active basis, ranges between about 1000:1 and 1:1000.

2. The combination of claim 1 wherein the weight ratio of a) to b) ranges between about 4:1 and 1:64.

3. A method for inhibiting microbial growth in an aqueous system which comprises adding to said system an effective amount of a synergistic antimicrobial combination comprising:
    a) 2,4,4'-trichloro-2'-hydroxydiphenyl ether; and
    b) 1,2-dibromo-2,4-dicyanobutane; wherein the weight ratio of a) to b), on an active basis, ranges between about 1000:1 and 1:1000.

4. The method of claim 3 wherein the weight ratio of a) to b), on an active basis ranges between about 4:1 and 1:64.

5. The method of claim 3 wherein the 2,4,4'-trichloro-2'-hydroxydiphenyl ether and 1,2-dibromo-2,4-dicyanobutane are added together as a single composition to the system being treated.

6. The method of claim 3 wherein the 2,4,4'-trichloro-2'-hydroxydiphenyl ether and 1,2-dibromo-2,4-dicyanobutane are added separately to the system being treated.

7. The method of claim 3 wherein at least 0.1 ppm of the synergistic antimicrobial composition is added to the system being treated.

8. The method of claim 3 wherein between about 50 ppm and 1000 ppm 2,4,4'-trichloro-2'-hydroxydiphenyl ether and between about 100 ppm and 500 ppm 1,2-dibromo-2,4-dicyanobutane are added to the system being treated.

9. A method of inhibiting microbial growth on an article of manufacture which comprises applying to said article an effective amount of a synergistic antimicrobial combination comprising:
    a) 2,4,4'-trichloro-2'-hydroxydiphenyl ether; and
    b) 1,2-dibromo-2,4-dicyanobutane compound; wherein the weight ratio of a) to b), on an active basis, ranges between about 1000:1 and 1:1000.

10. The method of claim 9 wherein the weight ratio of a) to b) ranges between about 4:1 and 1:64.

11. The method of claim 9 wherein the 2,4,4'-trichloro-2'-hydroxydiphenyl ether and 1,2-dibromo-2,4-dicyanobutane are applied together as a single composition to the article being treated.

12. The method of claim 9 wherein the 2,4,4'-trichloro-2'-hydroxydiphenyl ether and 1,2-dibromo-2,4-dicyanobutane are applied separately to the article being treated.

13. The method of claim 9 wherein said synergistic antimicrobial composition has a concentration of at least 0.1 ppm.

* * * * *

UNITED STATES PATENT AND TRADEMARK OFFICE
CERTIFICATE OF CORRECTION

PATENT NO. : 5,985,934
DATED : November 16, 1999
INVENTOR(S) : Tammy W. Gafney et al.

It is certified that error appears in the above-identified patent and that said Letters Patent is hereby corrected as shown below:

Column 3,
Line 27, "insention" should read -- invention --.

Column 4,
Line 60, "bc" should read -- be --.

Column 5,
Line 30, "Klebsiellapneumoniae" should read -- Klebsiella pneumoniae --.

Column 9,
Line 9, "dissoling" should read -- dissolving --.
Line 63, place a comma (,) between "basis" and "ranges".

Column 10,
Line 63, eliminate the space between "1" and ",2".

Signed and Sealed this

Eleventh Day of December, 2001

Attest:

NICHOLAS P. GODICI
Attesting Officer   Acting Director of the United States Patent and Trademark Office